United States Patent
Zhu et al.

(10) Patent No.: US 9,695,412 B2
(45) Date of Patent: Jul. 4, 2017

(54) SINGLE CELL ARRAY MICROCHIP AND FABRICATION, ELECTRICAL MEASUREMENT AND ELECTROPORATION METHOD THEREOF

(71) Applicant: TSINGHUA UNIVERSITY, Beijing (CN)

(72) Inventors: Rong Zhu, Beijing (CN); Xiaoliang Guo, Beijing (CN)

(73) Assignee: Tsinghua University, Beijing (CN)

( * ) Notice: Subject to any disclaimer, the term of this patent is extended or adjusted under 35 U.S.C. 154(b) by 147 days.

(21) Appl. No.: 14/328,425

(22) Filed: Jul. 10, 2014

(65) Prior Publication Data

US 2014/0323351 A1     Oct. 30, 2014

Related U.S. Application Data

(63) Continuation of application No. PCT/CN2013/070613, filed on Jan. 17, 2013.

(30) Foreign Application Priority Data

May 16, 2012 (CN) .......................... 2012 1 0152137

(51) Int. Cl.
  *C12M 1/34* (2006.01)
  *C12N 13/00* (2006.01)
  (Continued)

(52) U.S. Cl.
  CPC ......... *C12N 13/00* (2013.01); *G01N 33/4836* (2013.01); *G01N 33/5005* (2013.01);
  (Continued)

(58) Field of Classification Search
  CPC ............... C12N 13/00; G01N 33/4836; G01N 33/5005; B01J 2219/00533;
  (Continued)

(56) References Cited

U.S. PATENT DOCUMENTS 6,689,594 B1 * 2/2004 Hanni ................ G01N 33/4836
                                                    435/287.1
2007/0105206 A1   5/2007 Lu et al. .................... 435/173.6
(Continued)

FOREIGN PATENT DOCUMENTS

CN    101614729    12/2009
CN    101693875    4/2010    .............. C12M 1/12
(Continued)

OTHER PUBLICATIONS

International Search Report issued in corresponding foreign application, pp. 1-4 (Nov. 21, 2013).

*Primary Examiner* — William H Beisner
(74) *Attorney, Agent, or Firm* — J. Peter Paredes; Rosenbaum IP, P.C.

(57) ABSTRACT

The present invention relates to single cell array micro-chips and fabrication, electrical measurement and electroporation method thereof. The single cell array microchip comprises a substrate (1), a plurality of positioning electrodes (2) formed in an array, a plurality of measuring electrode-pairs (3) formed in an array, and a micro sample pool (4). The invention integrates cell array positioning with electrical measurement and electroporation for living cells, which is characteristic of label-free and noninvasive methods to manipulate, position particles/cells as well as further measure their electrical parameters. Therefore, single-cell-array positioning and multi-mode in-situ real-time measurement can be realized for intensive analysis. Since the positioned cells are immobile, the precision of the electrical measurement of cells is effectively improved, so is the efficiency of electroporation with lower cell mortality rate.

20 Claims, 3 Drawing Sheets

(51) Int. Cl.
  *G01N 33/50* (2006.01)
  *G01N 33/483* (2006.01)

(52) U.S. Cl.
  CPC ............... *B01J 2219/00533* (2013.01); *B01J 2219/00653* (2013.01); *B01J 2219/00743* (2013.01)

(58) Field of Classification Search
  CPC ... B01J 2219/00653; B01J 2219/00743; B01L 2300/0645
  USPC ..................................................... 435/287.1
  See application file for complete search history.

(56) References Cited

U.S. PATENT DOCUMENTS

| | | | |
|---|---|---|---|
| 2010/0270176 A1* | 10/2010 | Xiang ................ | G01N 33/4836 205/777.5 |
| 2011/0076734 A1 | 3/2011 | Zhou et al. ................ | 435/173.1 |
| 2011/0208029 A1 | 8/2011 | Joucla et al. ................ | 600/373 |

FOREIGN PATENT DOCUMENTS

| | | | | |
|---|---|---|---|---|
| CN | 101713757 | 5/2010 | ............ | C12M 1/34 |
| CN | 102174388 | 9/2011 | ............ | C12M 1/42 |
| CN | 102680526 | 9/2012 | ............ | G01N 27/00 |

\* cited by examiner

SINGLE CELL ARRAY MICROCHIP AND FABRICATION, ELECTRICAL MEASUREMENT AND ELECTROPORATION METHOD THEREOF

CROSS-REFERENCE TO RELATED APPLICATIONS

The present application claims priority from and is a continuation from PCT Application No. PCT/CN2013/070613, filed Jan. 17, 2013; which claims priority from Chinese Patent No. CN 201210152137.X, filed May 16, 2012, all herein incorporated by reference in their entireties.

TECHNICAL FIELD

The present invention relates the field of bio-detection technologies, and particularly relates to a single cell array microchip and fabrication, electrical measurement and electroporation method thereof.

BACKGROUND

Cells are recognized as basic elements of the activities of life, as a result of which the measurement and study of cells has aroused great attention in scientific research and medical field. Cell measurements according to their principles and approaches may include but are not limited to biomechanics measurement, electrical measurements, motility and physicochemical property measurement. The common methods adapted are acknowledged as observation via microscope, electrochemical measurement and optical measurement. To be observed via microscope and optically measurement, the cells need to be labeled chemically or fluorescently, which in turn changes the original properties of cells to some degree. Besides, the operation process is complicated and the function is limited to one single purpose. On the contrary, electrochemical measurement doesn't require labeling and does less harm to cells, which makes it possible to continuously measure the cells in a naturally culturing and real-time way. Comparing with conventional chemical methods, electrochemical measurement comes with higher sensitivity and full automation.

In terms of electrochemical measurement, it is essential to position the cells for implementing precise in-situ single cell assay. Dielectrophoresis (DEP) is given prominence as a significant manipulation tool for the studies of cells, viruses, DNA in the field of life science.

Existent technologies concerning cell electrical measurement don't position the cells, on account of which the cells are scattered randomly in the measurement process. Consequently the efficiency and precision of the measurement is difficult to compliment. The situation is same with electroporation. Furthermore, the random cell distribution on the chip brings about high cell mortality rate and poor controllability.

SUMMARY OF THE INVENTION

Provided herein are systems, methods and compositions foran apparatus comprising: a single cell array microchip comprising: a substrate; a plurality of positioning electrodes formed in an array; a plurality of measuring electrode-pairs formed in an array; a micro sample pool; wherein each four adjacent positioning electrodes form a shape of a rhombus functioning as a positioning unit; each row of the plurality of positioning electrodes are connected by lateral bars, or in the plurality of positioning electrodes formed in an array, the two pairs of the opposite positioning electrodes in each positioning unit are connected with the positioning electrodes in an adjacent positioning unit by the lateral bars and the longitudinal bars respectively; a measuring electrode pair is situated at the center of each positioning unit; the two measuring electrodes in each measuring electrode pair are connected with an electrode in an adjacent measuring electrode pair by the lateral bars and the longitudinal bars respectively.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE INVENTION

Figure 1:
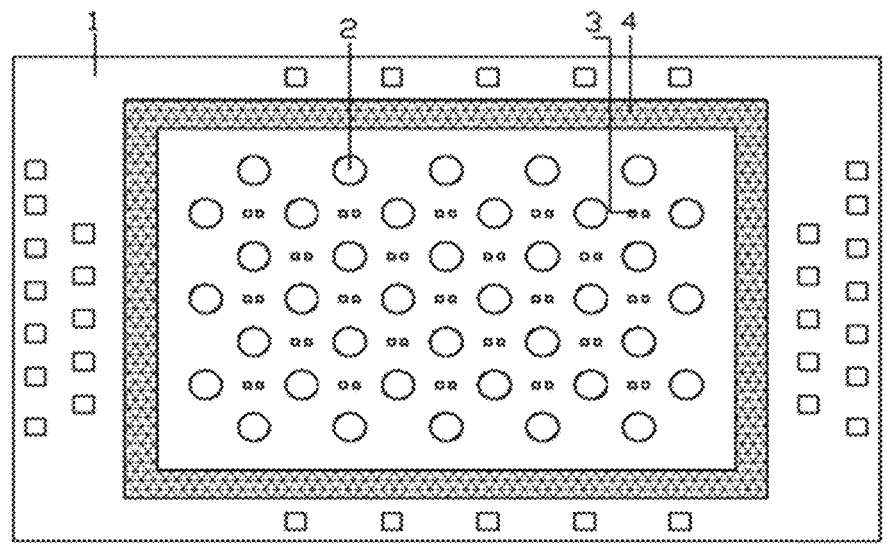
FIG. 1 is the structure schematic of the single cell array microchip of the present invention.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof (1) Technological Problems to be Solved The invention aims to provide a single-cell array microchip and fabrication, electrical measurement and electroporation method thereof, thus not only can the efficiency and precision of electrical measurement of single cells be improved effectively but the cell mortality rate due to electroporation can be decreased with better controllability as well.

(2) Technological Solution

According to one aspect of the present invention a microchip for single cell assay is provided to solve the problems above. The microchip is composed of a substrate; a plurality of positioning electrodes which form an array; an array of measuring electrode-pairs; a micro sample pool. Each four of the adjacent positioning electrodes form a shape of a rhombus functioning as one positioning unit.

In one embodiment, the electrodes in each row of the positioning electrodes array are connected by a lateral bar;

in another embodiment, the two pairs of opposite electrodes of each positioning unit are connected with other positioning electrodes in adjacent positioning unit by a longitudinal and a lateral bar respectively. At the centre of the recited positioning unit lies a pair of measuring electrodes; one of measuring electrodes in pair is connected with the adjacent measuring electrodes in other pairs by the longitudinal bar and the other measuring electrode in the mentioned pair by the lateral bar. The longitudinal bars and the lateral bars are patterned in different layers with an insulating layer in between. The substrate is one sort of insulating material or silicon covered with an insulating layer. The micro pool is constructed with a material of polymer or glass.

A method for producing the single cell array microchip comprises:

A. depositing a first metal layer on an insulating substrate, and etching the first metal layer to form longitudinal bars;

B. depositing a first insulating layer, and etching the first insulating layer to open a window of electrodes;

C. depositing a second metal layer, and etching the second metal layer to form lateral bars;

D. depositing a second insulating layer, and etching the second insulating layer to open a window of electrodes;

E. depositing a third metal layer, and etching the third metal layer to form positioning electrodes and the measuring electrode-pairs;

F. adhering a micro sample pool on the microchip.

A method for electrical measuring a cell by the single cell array microchip comprises:

Step 1. loading the sample of cell suspension into the micro sample pool;

Step 2. applying an alternating current (AC) signal to the positioning electrodes to exert negative DEP force on the cells, and moving the cells to the region with the minimal electrical field intensity;

Step 3. measuring the current signal through two electrodes of each measuring electrode-pair in the array individually while applying a bias voltage between them by a scanning method in longitudinal and lateral directions respectively;

Step 4. measuring the current signal of the measuring electrode pair to decide if there is a cell positioned thereon;

Step 5. measuring the current signal with a bias voltage applied between the decided measuring electrode-pair with a cell.

As mentioned in Step 4, to decide if there is a cell on the measuring electrodes, the current signal calibration is needed in advance to obtain the current ranges with and without cell positioned.

Based on the aforementioned single-cell array microchip, a method of electroporation comprises:

Step 11. loading the sample of cell suspension into the micro sample pool;

Step 22. applying an alternating current (AC) signal to the positioning electrodes to exert negative DEP force on the cells, and moving the cells to the region with the minimal electrical field intensity;

Step 33. measuring the current signal through two electrodes of each measuring electrode-pair in the array individually while applying a bias voltage between them by a scanning method in longitudinal and lateral directions respectively;

Step 44. measuring the current signal of the measuring electrode pair to decide if there is a cell positioned thereon.

Step 55. implementing the cell electroporation by applying a pulse voltage signal to the decided measuring electrode-pair with a cell.

As mentioned in Step 44, to decide if there is a cell on the measuring electrodes, the current signal calibration is needed in advance to obtain the current ranges with and without cell positioned.

(3) Beneficial Effects

The invention integrates cell array positioning with electrical measurement and electroporation for living cells, which is characteristic of label-free and noninvasive methods to manipulate, position particles/cells as well as further measure their electrical parameters. Therefore, single-cell-array positioning and multi-mode in-situ real-time measurement can be realized for intensive analysis. Since the positioned cells are immobile, the precision of the electrical measurement of cells is effectively improved, so is the efficiency of electroporation with lower cell mortality rate. The present invention also introduces automation and control technology into cell manipulation and electrical measurement. With the feedback of electrical measurement, cell positioning can be controlled automatically, which facilitates the rapid, accurate and multi-mode measurement and analysis of cells.

Specific representative embodiments of the invention will now be further described according to the drawings and examples. It is understood that the method, materials, conditions, process parameters and the like do not necessarily limit the scope of the invention.

EXAMPLE 1

Figure 2:
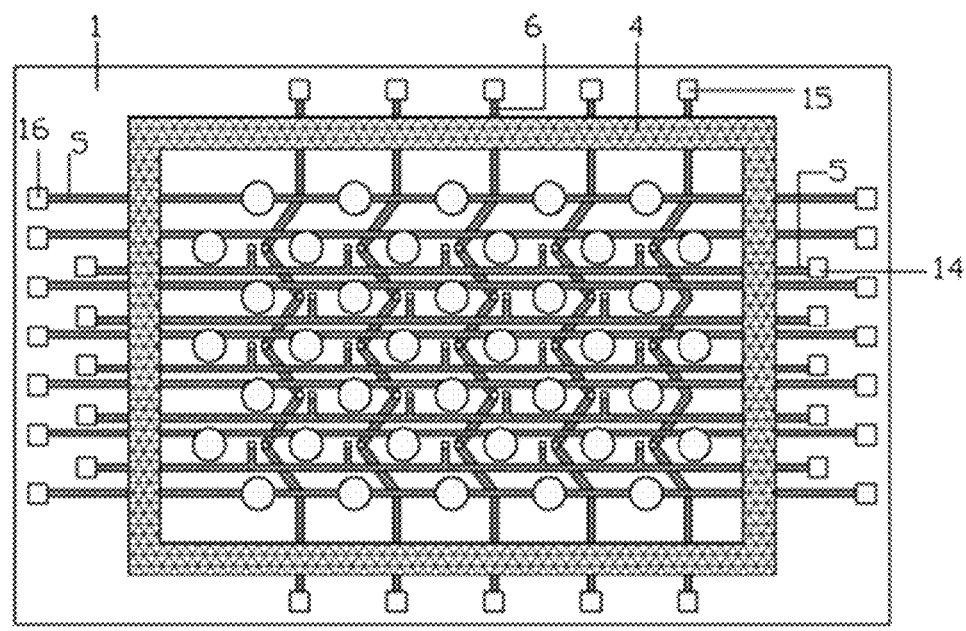
FIG. 2 is the structure schematic of the electrode connecting bars, in accordance with the first embodiment of the present invention.

As is illustrated in FIG. 1 and FIG. 2, the present invention provides a single cell array microchip, comprising a substrate 1; a plurality of positioning electrodes which form an array 2; an array of measuring electrode-pairs 3; a micro sample pool 4. Each four adjacent positioning electrodes 2 form a shape of a rhombus functioning as one positioning unit. At the centre of the recited positioning unit lies a pair of measuring electrodes 3. Each row of the multiple positioning electrodes 2 are connected by lateral bars 5. Two electrodes in each measuring electrode pair 3 are connected with an electrode in an adjacent measuring electrode pair by the longitudinal bar 6 and the lateral bar 5 respectively.

The lateral bars 5 and the longitudinal bars 6 are patterned in different layers with an insulating layer in between.

The substrate 1 is made of an insulating material, such as glass, or silicon covered with an insulating layer. The micro sample pool 4 is constructed with polydimethylsiloxane (PDMS). The insulating layer is made of $Si_3N_4$, $SiO_2$ or other polymer material. The micro sample pool can be fabricated with a mold or by way of other machining methods. For the lateral bars of measuring electrode-pairs 3, the electrical signal is inputted and outputted via the bonding pad 14, and for the longitudinal bars of measuring electrode-pairs 3, the electrical signal is inputted and outputted via the bonding pad 15; for the lateral bars of positioning electrodes 2, the electrical signal is merely inputted via bonding pad 16.

EXAMPLE 2

Figure 3:
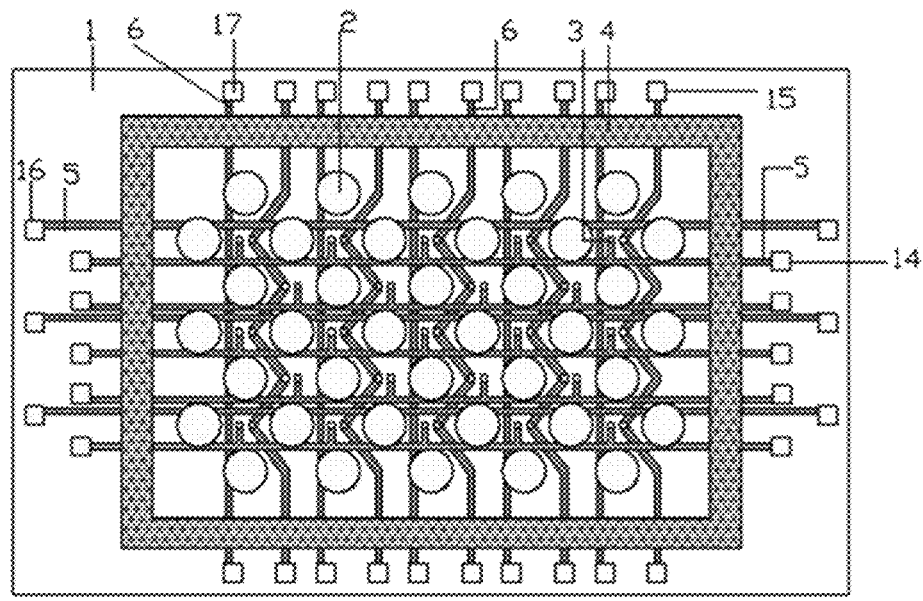
FIG. 3 is the structure schematic of the electrode connecting bars, in accordance with the second embodiment of the present invention.
Figure 4A:
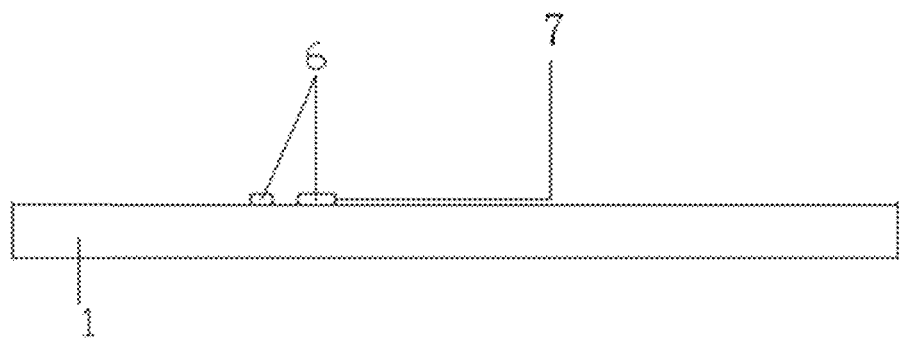
FIGS. 4a-4f illustrates the fabrication process of single cell array microchip, in accordance with the third embodiment of the present invention.
Figure 4B:
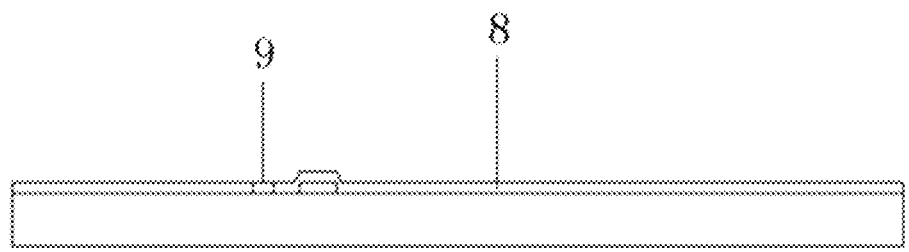
Figure 4C:
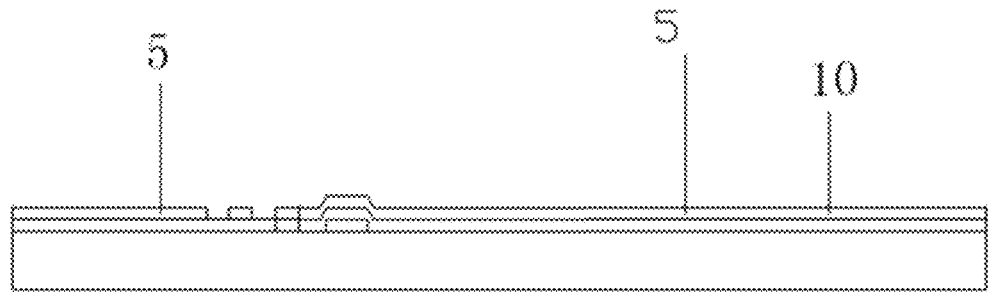
Figure 4D:
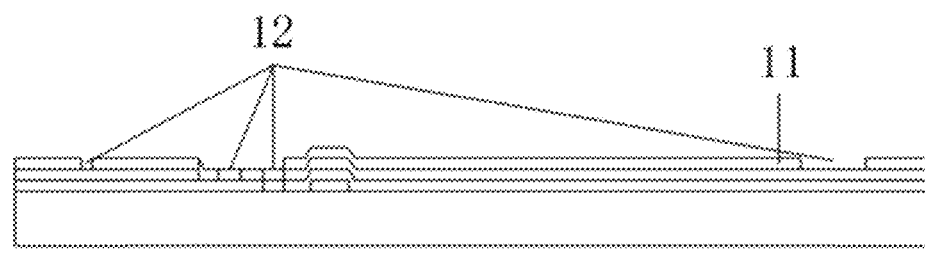
Figure 4E:
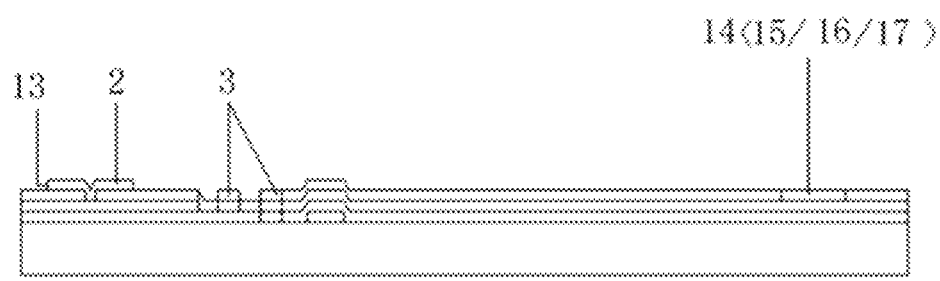
Figure 4F:
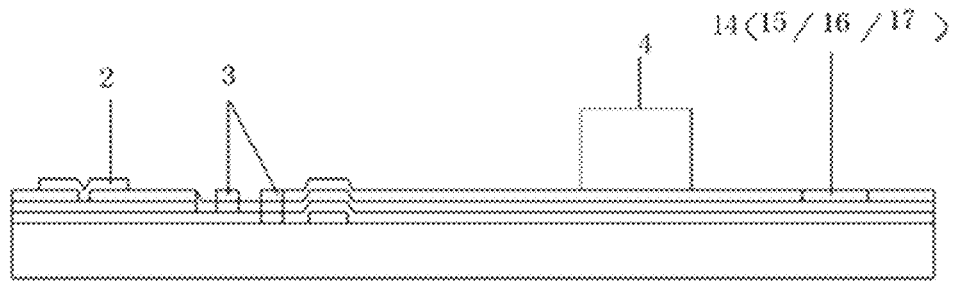

FIG. 3 shows another embodiment of the present invention which is different from embodiment 1 in the layout of the connecting bars of the positioning electrodes 2. As can be seen from the drawing, the two pairs of the opposite electrodes in each positioning unit are connected with other positioning electrodes in adjacent positioning unit by longitudinal 6 and lateral bars 5 respectively. For the lateral bars of positioning electrodes, the electrical signal is inputted and outputted via the bonding pad 16, and for the longitudinal bars of positioning electrodes, the electrical signal is inputted and outputted via the bonding pad 17.

EXAMPLE 3

FIGS. 4a-4f illustrate the fabrication process of single cell array microchip according to one aspect of the present invention. A glass substrate is employed to fulfill the fabrication with the following steps orderly.

a. The first layer of Ti/Au 7 is sputtered on the glass substrate 1, followed by the lithography process to pattern the longitudinal electrode bars 6.

b. The first insulating layer of $SiO_2$ 8 is deposited and etched to open the window of electrodes (and the bonding pads) 9.

c. The second layer of Ti/Au 10 is deposited, followed by the lithography process to pattern the lateral electrode bars 5.

d. The second insulating layer of $SiO_2$ 11 is deposited and etched to open the window of electrodes (and the bonding pads) 12.

e. The third layer of Ti/Au 13 is deposited, followed by the lithography process to pattern the positioning electrodes 2 and the measuring electrode-pairs 3 and bonding pads 14, 15, 16, 17.

f. The micro sample pool 4 is sequentially constructed by adhesion of the micro sample pool on the microchip to ensure that positioning electrodes 2 and the measuring electrode-pairs 3 are inside the pool and the bonding pads 14, 15, 16, 17 are outside.

EXAMPLE 4

A method of electrical measurement by means of the mentioned device of single cell array microchips is elucidated as to the following steps:

Step 1: The sample suspension of cells is injected into the micro sample pool 4.

Step 2: An alternating current (AC) signal is applied to the positioning electrodes 2 to exert negative DEP force on the cells, resulting in the motion of cells to the region with the minimal electrical field intensity. Specifically, the opposite electrodes in each positioning unit are applied with the same sinusoidal signals while the adjacent electrodes in the unit vary with a phase difference of 180°. The region with minimal electrical field intensity is located at the centre of the mentioned positioning unit.

Step 3: Individually measure the current signal through two electrodes of each measuring electrode-pair in the array while applying a bias voltage between them by a scanning method in longitudinal and lateral directions respectively.

Step 4: The current signal of the measuring electrode pair 3 is measured to decide if there is a cell positioned thereon. To decide if there is a cell on the measuring electrode pairs according to the current signal, beforehand calibration is needed to obtain the current ranges with and without cell positioned. If the current measured is within the range corresponding to the condition with cells positioned, we can draw that conclusion or vice versa.

Step 5: Eventually the current signal is measured with a bias voltage applied between the decided measuring electrode-pair with a cell. The voltage signal applied to measuring electrodes can be direct current, alternating current or pulse voltage signal.

EXAMPLE 5

A method of electroporation by means of the mentioned device of single cell array microchips is elucidated as to the following steps:

Step 11: The sample suspension of cells is injected into the micro sample pool 4.

Step 22: An alternating current (AC) signal is applied to the positioning electrodes 2 to exert negative DEP force on the cells, resulting in the motion of cells to the region with the minimal electrical field intensity. Specifically, the opposite electrodes in each positioning unit are applied with the same sinusoidal signals while the adjacent electrodes distributed in the unit vary with a phase difference of 180°. The region with minimal electrical field intensity is located at the centre of the mentioned positioning unit.

Step 33: Individually measure the current signal through two electrodes of each measuring electrode-pair in the array while applying a bias voltage between them by a scanning method in longitudinal and lateral directions respectively.

Step 44: The current signal of the measuring electrode pair 3 is measured to decide if there is a cell positioned thereon. To decide if there is a cell on the measuring electrode pairs according to the current signal, beforehand calibration is needed to obtain the current ranges with and without a single cell positioned. If the current measured is within the range corresponding to the condition with cells positioned, we can draw that conclusion or vice versa.

Step 55: The cell electroporation is implemented by applying a pulse voltage signal to the decided measuring electrode-pair with a cell.

It is understood that the various embodiments described herein are by way of example only, and are not intended to limit the scope of the invention. Although specific embodiments of the invention are described for purposes of illustration, various modifications and changes may be made by those skilled in the art without deviating from the spirit and scope of the invention. The scope of the invention is, therefore, indicated by the appended claims rather than by the foregoing descriptions. All changes which come within the meaning and range of equivalency of the claims are to be embraced within the scope.

INDUSTRIAL PRACTICABILITY

The invention integrates cell array positioning with electrical measurement and electroporation for living cells, which is characteristic of label-free and noninvasive methods to manipulate, position particles/cells as well as further measure their electrical parameters. Therefore, single-cell-array positioning and multi-mode in-situ real-time measurement can be realized for intensive analysis. Since the positioned cells are immobile, the precision of the electrical measurement of cells is effectively improved, so is the efficiency of electroporation with lower cell mortality rate. The present invention also introduces automation and control technology into cell manipulation and electrical measurement. With the feedback of electrical measurement, cell positioning can be controlled automatically, which facilitates the rapid, accurate and multi-mode measurement and analysis of cells.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. An apparatus comprising:

A single cell array microchip comprising: a substrate; a plurality of positioning electrodes formed in an array; a plurality of measuring electrode-pairs formed in an array; a micro sample pool positioned on a surface of the substrate and creating a barrier around the plurality of positioning electrodes and measuring electrode pairs; wherein each four adjacent positioning electrodes form a shape of a rhombus functioning as a positioning unit;

the plurality of positioning electrodes in each row are connected by to one another by a lateral bar, or in the plurality of positioning electrodes formed in an array, the two pairs of the opposite positioning electrodes in each positioning unit are connected with the positioning electrodes in an adjacent positioning unit by a lateral bar and a longitudinal bar respectively;

a measuring electrode pair is situated at the center of each positioning unit; the two measuring electrodes in each measuring electrode pair are connected with an electrode in an adjacent measuring electrode pair by a lateral bar and a longitudinal bar respectively; wherein each lateral bar and longitudinal bar is electrically insulated from other lateral and longitudinal bars on the substrate.

2. The single cell array microchip according to claim 1, wherein the longitudinal bars and the lateral bars are patterned in different layers with an insulating layer in between.

3. A method for producing a single cell array microchip according to claim 2 comprising:

A. depositing a first metal layer on an insulating substrate, and etching the first metal layer to form longitudinal bars;

B. depositing a first insulating layer, and etching the first insulating layer to open a window of electrodes;

C. depositing a second metal layer, and etching the second metal layer to form lateral bars;

D. depositing a second insulating layer, and etching the second insulating layer to open a window of electrodes;

E. depositing a third metal layer, and etching the third metal layer to form positioning electrodes and the measuring electrode-pairs;

F. adhering a micro sample pool on the microchip.

4. A method for electrical measuring a cell by the single cell array microchip according to claim 2, comprising:

S1. loading a cell suspension into the micro sample pool;

S2. applying an alternating current (AC) signal to the positioning electrodes to exert negative DEP force on the cells, and moving the cells to the region with the minimal electrical field intensity;

S3. measuring the current signal through two electrodes of each measuring electrode-pair in the array individually while applying a bias voltage between two electrodes of each measuring electrode-pair by a scanning method in longitudinal and lateral directions respectively;

S4. measuring the current signal of the measuring electrode pair to decide if there is a cell positioned on the electrodes of the measuring electrode pair; and S5. measuring the current signal with a bias voltage applied between the two electrodes of the measuring electrode-pair positioned with a cell.

5. A method of electroporation by the single cell array microchip according to claim 2 comprising:

S11. loading a cell suspension into the micro sample pool;

S22. applying an alternating current (AC) signal to the positioning electrodes to exert negative DEP force on the cells, and moving the cells to the region with the minimal electrical field intensity;

S33. measuring the current signal through two electrodes of each measuring electrode-pair in the array individually while applying a bias voltage between them by a scanning method in longitudinal and lateral directions respectively;

S44. measuring the current signal of the measuring electrode pair to decide if there is a cell positioned on the electrodes of the measuring electrode pair; and S55. implementing the cell electroporation by applying a pulse voltage signal to the decided measuring electrode-pair with a cell.

6. The method of electroporation according to claims 5, wherein Step S44 further comprising: beforehand calibrating current signal to obtain the current ranges with and without a single cell positioned for the purpose of deciding the measuring electrode-pair whether there is a cell positioned thereon according to the results of calibration.

7. The single cell array microchip according to claim 1, wherein the substrate is an insulating material or a silicon material covered with an insulating layer.

8. A method for producing a single cell array microchip according to claim 7 comprising:

A. depositing a first metal layer on an insulating substrate, and etching the first metal layer to form longitudinal bars;

B. depositing a first insulating layer, and etching the first insulating layer to open a window of electrodes;

C. depositing a second metal layer, and etching the second metal layer to form lateral bars;

D. depositing a second insulating layer, and etching the second insulating layer to open a window of electrodes;

E. depositing a third metal layer, and etching the third metal layer to form positioning electrodes and the measuring electrode-pairs;

F. adhering a micro sample pool on the microchip.

9. A method for electrical measuring a cell by the single cell array microchip according to claim 7, comprising:

S1. loading a cell suspension into the micro sample pool;

S2. applying an alternating current (AC) signal to the positioning electrodes to exert negative DEP force on the cells, and moving the cells to the region with the minimal electrical field intensity;

S3. measuring the current signal through two electrodes of each measuring electrode-pair in the array individually while applying a bias voltage between two electrodes of each measuring electrode-pair by a scanning method in longitudinal and lateral directions respectively;

S4. measuring the current signal of the measuring electrode pair to decide if there is a cell positioned on the electrodes of the measuring electrode pair; and S5. measuring the current signal with a bias voltage applied between the two electrodes of the measuring electrode-pair positioned with a cell.

10. A method of electroporation by the single cell array microchip according to claim 7 comprising:

S11. loading a cell suspension into the micro sample pool;

S22. applying an alternating current (AC) signal to the positioning electrodes to exert negative DEP force on the cells, and moving the cells to the region with the minimal electrical field intensity;

S33. measuring the current signal through two electrodes of each measuring electrode-pair in the array individually while applying a bias voltage between them by a scanning method in longitudinal and lateral directions respectively;

S44. measuring the current signal of the measuring electrode pair to decide if there is a cell positioned on the electrodes of the measuring electrode pair; and S55. implementing the cell electroporation by applying a pulse voltage signal to the decided measuring electrode-pair with a cell.

11. The method of electroporation according to claims 10, wherein Step S44 further comprising: beforehand calibrating current signal to obtain the current ranges with and without a single cell positioned for the purpose of deciding the measuring electrode-pair whether there is a cell positioned thereon according to the results of calibration.

12. The single cell array microchip according to claim 1, wherein the micro sample pool is a polymer material or a glass material.

13. A method for producing a single cell array microchip according to claim 12 comprising:
   A. depositing a first metal layer on an insulating substrate, and etching the first metal layer to form longitudinal bars;
   B. depositing a first insulating layer, and etching the first insulating layer to open a window of electrodes;
   C. depositing a second metal layer, and etching the second metal layer to form lateral bars;
   D. depositing a second insulating layer, and etching the second insulating layer to open a window of electrodes;
   E. depositing a third metal layer, and etching the third metal layer to form positioning electrodes and the measuring electrode-pairs;
   F. adhering a micro sample pool on the microchip.

14. A method for electrical measuring a cell by the single cell array microchip according to claim 12, comprising:
   S1. loading a cell suspension into the micro sample pool;
   S2. applying an alternating current (AC) signal to the positioning electrodes to exert negative DEP force on the cells, and moving the cells to the region with the minimal electrical field intensity;
   S3. measuring the current signal through two electrodes of each measuring electrode-pair in the array individually while applying a bias voltage between two electrodes of each measuring electrode-pair by a scanning method in longitudinal and lateral directions respectively;
   S4. measuring the current signal of the measuring electrode pair to decide if there is a cell positioned on the electrodes of the measuring electrode pair; and
   S5. measuring the current signal with a bias voltage applied between the two electrodes of the measuring electrode-pair positioned with a cell.

15. A method of electroporation by the single cell array microchip according to claim 12 comprising:
   S11. loading a cell suspension into the micro sample pool;
   S22. applying an alternating current (AC) signal to the positioning electrodes to exert negative DEP force on the cells, and moving the cells to the region with the minimal electrical field intensity;
   S33. measuring the current signal through two electrodes of each measuring electrode-pair in the array individually while applying a bias voltage between them by a scanning method in longitudinal and lateral directions respectively;
   S44. measuring the current signal of the measuring electrode pair to decide if there is a cell positioned on the electrodes of the measuring electrode pair; and
   S55. implementing the cell electroporation by applying a pulse voltage signal to the decided measuring electrode-pair with a cell.

16. A method for producing a single cell array microchip according to claim 1 comprising:
   A. depositing a first metal layer on an insulating substrate, and etching the first metal layer to form longitudinal bars;
   B. depositing a first insulating layer, and etching the first insulating layer to open a window of electrodes;
   C. depositing a second metal layer, and etching the second metal layer to form lateral bars;
   D. depositing a second insulating layer, and etching the second insulating layer to open a window of electrodes;
   E. depositing a third metal layer, and etching the third metal layer to form positioning electrodes and the measuring electrode-pairs;
   F. adhering a micro sample pool on the microchip.

17. A method for electrical measuring a cell by the single cell array microchip according to claim 1, comprising:
   S1. loading a cell suspension into the micro sample pool;
   S2. applying an alternating current (AC) signal to the positioning electrodes to exert negative DEP force on the cells, and moving the cells to the region with the minimal electrical field intensity;
   S3. measuring the current signal through two electrodes of each measuring electrode-pair in the array individually while applying a bias voltage between two electrodes of each measuring electrode-pair by a scanning method in longitudinal and lateral directions respectively;
   S4. measuring the current signal of the measuring electrode pair to decide if there is a cell positioned on the electrodes of the measuring electrode pair; and
   S5. measuring the current signal with a bias voltage applied between the two electrodes of the measuring electrode-pair positioned with a cell.

18. The method for electrical measuring a cell according to claim 17, wherein Step S4 further comprising: beforehand calibrating current signal to obtain the current ranges with and without a single cell positioned for the purpose of deciding the measuring electrode-pair whether there is a cell positioned thereon according to the results of calibration.

19. A method of electroporation by the single cell array microchip according to claim 1 comprising:
   S11. loading a cell suspension into the micro sample pool;
   S22. applying an alternating current (AC) signal to the positioning electrodes to exert negative DEP force on the cells, and moving the cells to the region with the minimal electrical field intensity;
   S33. measuring the current signal through two electrodes of each measuring electrode-pair in the array individually while applying a bias voltage between them by a scanning method in longitudinal and lateral directions respectively;
   S44. measuring the current signal of the measuring electrode pair to decide if there is a cell positioned on the electrodes of the measuring electrode pair; and
   S55. implementing the cell electroporation by applying a pulse voltage signal to the decided measuring electrode-pair with a cell.

20. The method of electroporation according to claims 19, wherein Step S44 further comprising: beforehand calibrating current signal to obtain the current ranges with and without a single cell positioned for the purpose of deciding the measuring electrode-pair whether there is a cell positioned thereon according to the results of calibration.

* * * * *